United States Patent
Agarwal et al.

(10) Patent No.: US 6,194,212 B1
(45) Date of Patent: Feb. 27, 2001

(54) VECTORS COMPRISING SAR ELEMENTS

(75) Inventors: Manju Agarwal; Ivan Plavec, both of Sunnyvale; Gabor Veres, Palo Alto, all of CA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/194,301

(22) PCT Filed: Jun. 6, 1997

(86) PCT No.: PCT/EP97/02972

§ 371 Date: Nov. 23, 1998

§ 102(e) Date: Nov. 23, 1998

(87) PCT Pub. No.: WO97/46687

PCT Pub. Date: Dec. 11, 1997

Related U.S. Application Data

(60) Provisional application No. 60/019,231, filed on Jun. 6, 1996.

(51) Int. Cl.$^7$ .................................................... C12N 15/86
(52) U.S. Cl. ................. 435/456; 435/366; 435/320.1
(58) Field of Search .................. 435/456, 69.1, 435/366, 372, 372.3, 320.1

(56) References Cited

FOREIGN PATENT DOCUMENTS

| WO 96/19573 | 6/1996 | (CA) . |
| WO 90/14427 | 11/1990 | (EP) . |
| WO 95/20653 | 8/1995 | (FR) . |

OTHER PUBLICATIONS

Bebec, D., et al., Proc. Natl. Acad. Sci., vol. 89, Oct. 1992, pp. 9870–9874.

Phi–Van, L., et al., Mol. Cell. Biol., vol. 10, No. 5, May 1990, pp. 2302–2307.

Plavec, I., et al., Gene Therapy, vol. 3, No. 8, Aug. 1996, pp. 717–724.

Plavec, I., et al., Gene Therapy, vol. 4, No. 2, Feb. 1997, pp. 128–139.

Rigg, R. J., et al. Virology, vol. 218, No. 1, Apr. 1996, pp. 290–295.

Mielke, C., et al., Biochem. vol. 29; 7475–7485 (1990).

Mielke et al., Biochem 35:2239–2252 (Feb. 20, 1996).

George et al., "Current methods in sequence comparison and analysis," in Macromolecular Sequencing and Synthesis, Selected methods and Applications, 1988, D.H. Schlesinger (ed.), Alan R. Liss, Inc. New York, NY, pp. 127–149.*

Boswell et al., "Sequence comparison and alignment: the measurement and interpretation of sequence similarity," in Computational Molecular Biology: Sources and Methods for Sequence Analysis, 1988, Arthur M. Lesk (ed.), Oxford University Press, New York, NY, pp. 161–178.*

McLachlin et al., Progress in Nucleic Acid Research and Molecular Biology 38:91–136 (1990).*

Escaich et al., Human Gene Therapy 6:625–634 (1995).*

Klehr et al., Biochemistry 30:1264–1270 (1991).*

* cited by examiner

Primary Examiner—Remy Yucel
(74) Attorney, Agent, or Firm—Geoffrey M. Karny

(57) ABSTRACT

This invention relates to a method of using scaffold attachment regions (SARs) to increase expression in retrovirally transduced resting cells. A particularly preferred SAR is the 5' SAR of the human interferon β gene or a fragment thereof having at least 450 base pairs.

53 Claims, 10 Drawing Sheets

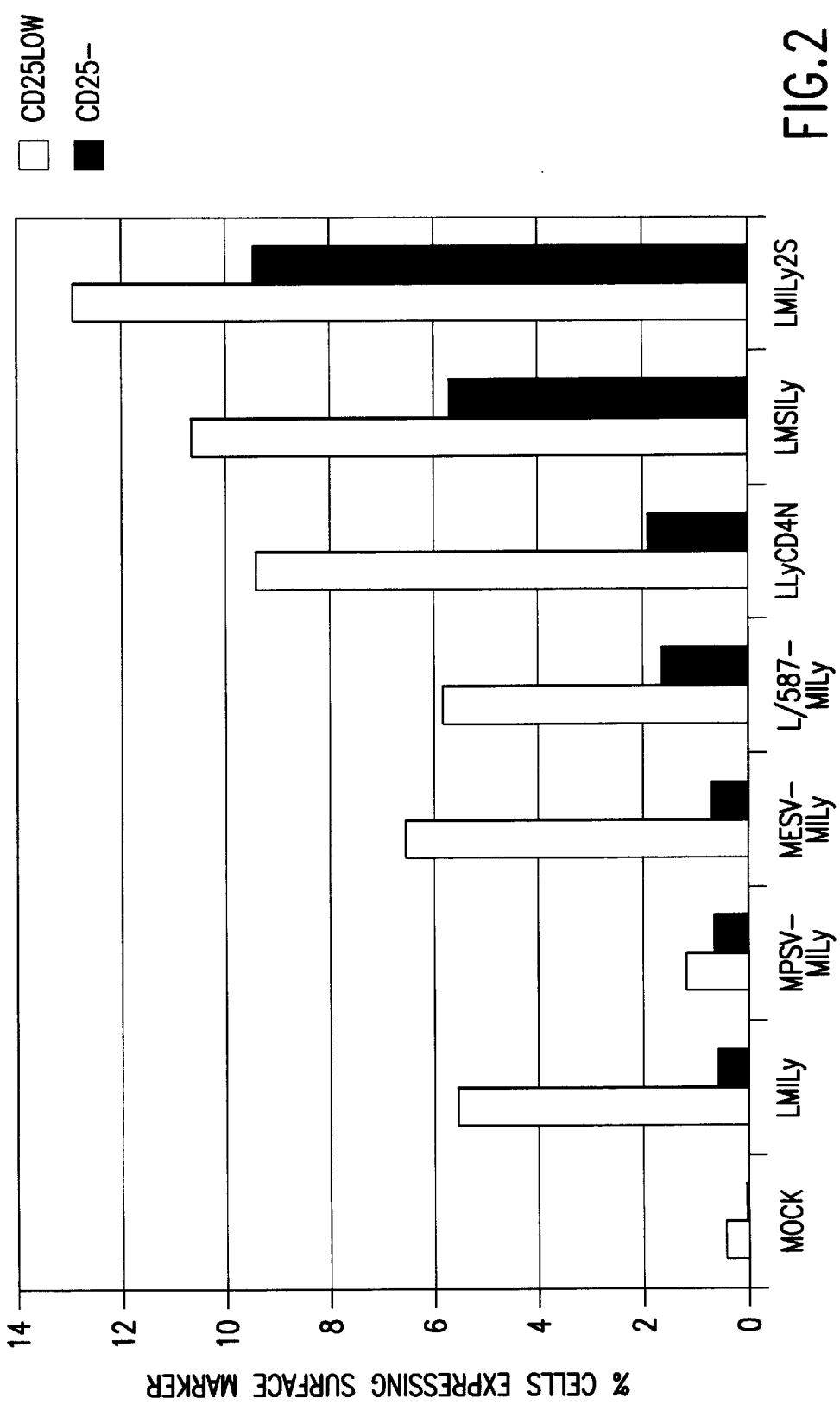

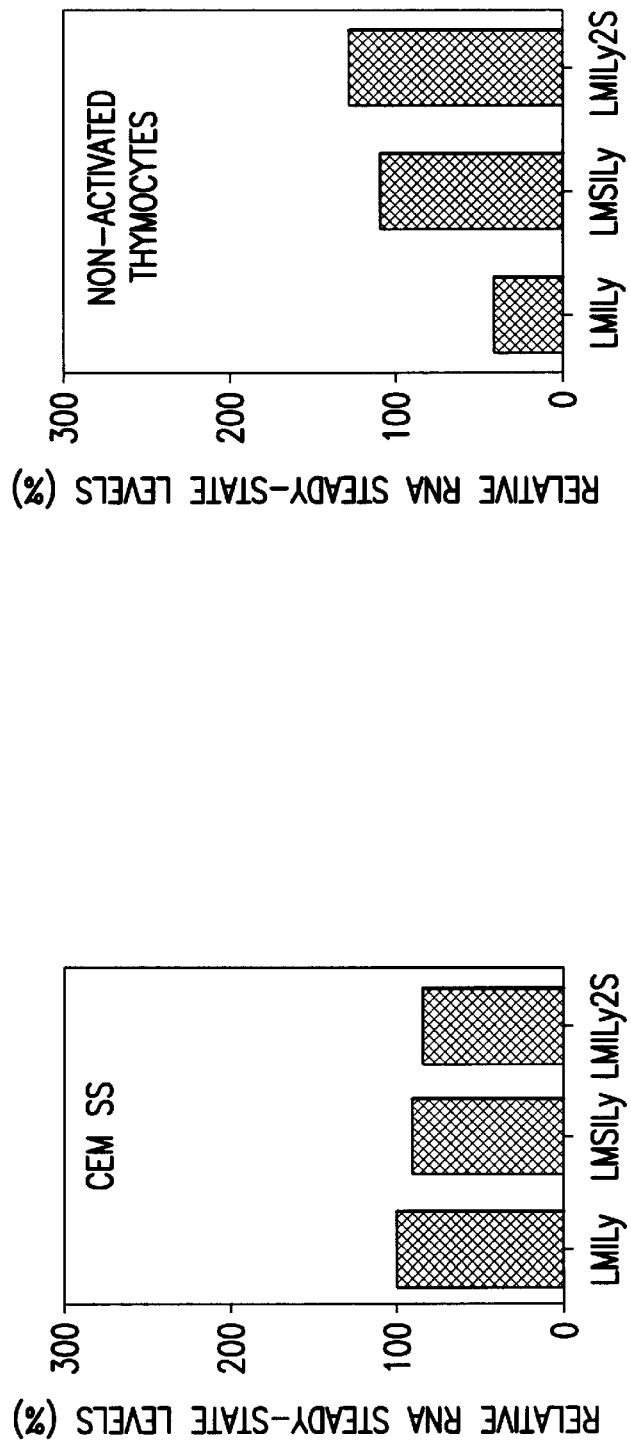

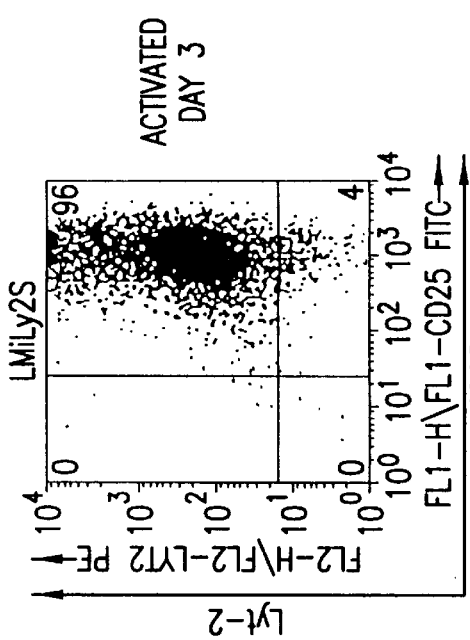
FIG. 8A MOCK
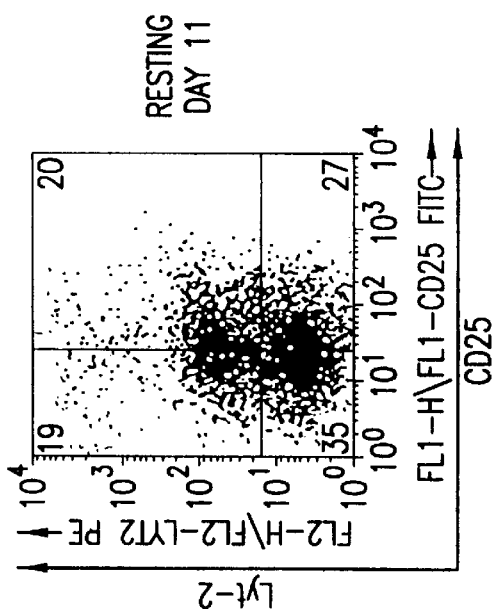
FIG. 8B LMiLy
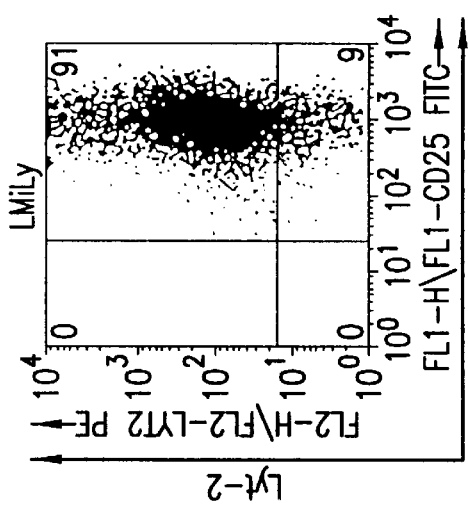
FIG. 8C LMiLy2S
ACTIVATED DAY 3
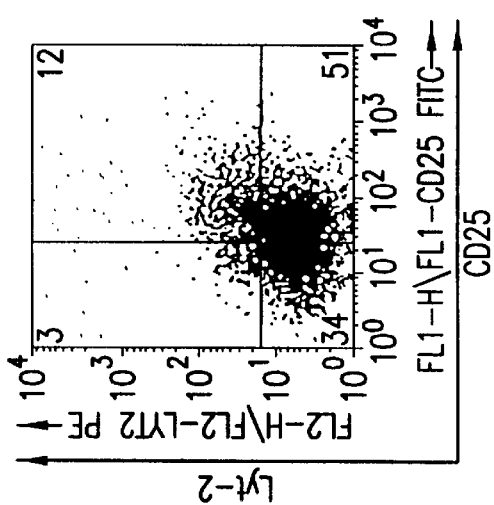
FIG. 8D
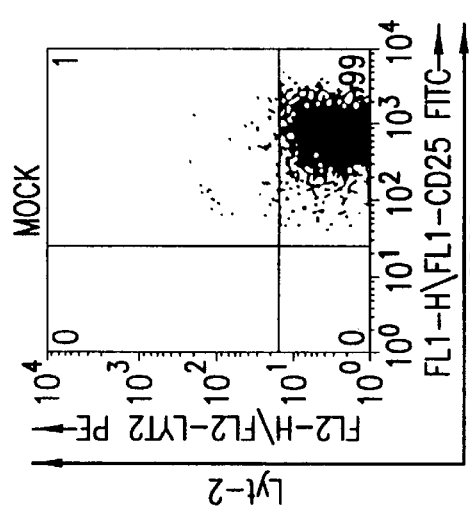
FIG. 8E
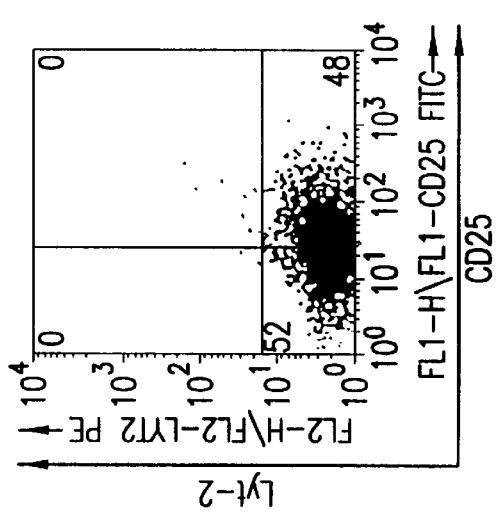
FIG. 8F
RESTING DAY 11

VECTORS COMPRISING SAR ELEMENTS

This application claims the benefit of U.S. Provisional application Ser. No. 60/019,231, filed Jun. 6, 1996 and U.S. application Ser. No. 08/660,018, filed Jun. 6, 1996, now abandoned.

This invention relates to the use of scaffold attachment regions (SARs) to increase gene expression in primary non-proliferating cells i.e. in resting cells.

Eukaryotic chromosomes are organised into discrete chromatin domains which are thought to define independent units encompassing all required cis-regulatory elements for co-ordinated expression of the genes within the domain. These chromatin domains are bordered by sequences which specifically associate with the nuclear scaffold, or nuclear matrix, defining the boundaries of the chromatin domains. Such sequences are referred to as scaffold attachment region (SAR) or matrix attachment region (MAR). SAR elements are several hundred basepairs long and A/T rich ($\geq 70\%$). Although cloned SAR and MAR elements share common structural features, no consensus sequence has been identified. SARs have been located upstream, downstream or within genes (introns) suggesting that they may represent functionally distinct classes (Bode J et al. 1995 *Scaffold/Matrix-attachment regions (S/MAR): Structural properties creating transcriptionally active loci* Academic Press, Orlando). SAR elements can enhance expression of heterologous genes in transfection experiments in vitro and in transgenic mice. In some instances, it has been reported that SAR elements can confer position-independent expression to a linked transgene.

While transfected DNA integrates randomly into chromosomes, there is growing evidence that retroviral integration is not completely random (Shih, C. C 1988 *Cell* 53, 531–537, Rohdewohld, H et al 1987 *J. Virol.* 61, 336–343 and Mielke, C et al 1996 *Biochemistry* 35, 2239–2252). Notably, proviruses preferentially integrate into host SAR sequences (Mielke, C et al 1996) and into "open" chromatin characterised by sensitivity to DNaseI digestion (Rohdewohld, H et al 1987).

Our experience has shown that the regulation of gene expression is different for resting cells as opposed to proliferating cells. We have found that gene expression of transduced genes is significantly decreased in resting (i.e. not mitotically active) cells as compared to active cells. Low expression in resting cells is a problem when expression is desired in vivo, e.g., in gene therapy, because at any given time, most cells in the body (unlike most cells in cell cultures) are in a quiescent state. Thus, although methods are now available to permit and enhance integration of heterologous genetic material into normal resting cells, there are at present no established ways to enhance expression of the heterologous genetic material in such cells.

One might suppose that the difference in expression is due to limiting quantities of necessary transcription factors or to control by specific promoter/enhancer elements. Our research suggests, however, that this difference in expression between resting and proliferating cells is largely due to changes in chromatin structure mediated by the DNA SARs. Hereinafter, use of the term SAR will be understood to encompass scaffold and matrix attachment regions.

We have now discovered that SARs increase expression of heterologous genes in transduced eukaryotic resting primary cells, particularly in retrovirally transduced cells. The SAR sequence has no detectable influence on retroviral vector expression in transduced cell lines. In contrast, the SAR-containing vectors express at significantly higher levels compared to controls in resting primary T cells. For example, we have shown that in retrovirally transduced resting primary T cells, a SAR significantly increases expression of the heterologous gene, both in terms of percentage of cells expressing that gene and in terms of levels of expression per cell. This is the first demonstration that retroviral mediated transduction of a SAR and a heterologous gene in cis improves expression of that gene, and the first demonstration that co-transduction with a SAR and a heterologous gene improves expression of the gene in resting primary cells.

Vectors suitable for use in the present invention are chosen on the basis of their ability of causing integration with the host genetic material. Accordingly, retroviruses which include oncoviruses such as Moloney C type and lentiviruses are suitable for purposes of the present invention. The invention may also be practised by introducing the DNA by homologous recombination or by using artificial human chromosomes.

The invention thus provides, in a first embodiment
  (i) Use of a SAR to increase gene expression in transduced cells for example resting cells, including resting progeny of transduced cells;
  (ii) A method of increasing expression of a heterologous gene in a resting cell comprising transducing a cell, e.g., a non-immortal cell, with (i) the heterologous gene and (ii) one or more SARs.

A SAR for use in the present invention is not itself transcribed and translated to express a protein, nor is it a promoter or enhancer element for a gene; its effect on gene expression is mostly position-independent. By position-independent is understood that the SAR is placed within the vector and is not placed so as to destroy other functions required for gene transfer and expression for example the SAR should not be inserted in a position which blocks an essential LTR function. Preferably the SAR is at least 450 base pairs (bp) in length, preferably from 600–1000 bp, e.g., about 800 bp. The SAR is preferably AT-rich (i.e., more than 50%, preferably more than 70% of the bases are adenine or thymine), and will generally comprise repeated 4–6 bp motifs, e.g., ATTA, ATTTA, ATTTTA, TAAT, TAAAT, TAAAAT, TAATA, and/or ATATTT, separated by spacer sequences, e.g., 3–20 bp, usually 8–12 bp in length. The SAR may be from any eukaryote, preferably a mammal, most preferably a human. Suitably the SAR is the SAR for human IFN-β gene or fragment thereof, e.g., preferably derived from or corresponding to the 5' SAR of human interpheron beta (IFN-β), Klehr, D et al. Scaffold-Attached Regions from the Human Interferon β domain Can Be Used To Enhance the Stable Expression of Genes under the Control of Various Promoters. Biochemistry 1991, 30, 1264–1270), e.g., a fragment of at least 450 base pairs (bp) in length, preferably from 600–1000 bp, e.g., about 800 bp, and being substantially homologous to a corresponding portion of the 5' SAR of human IFN-β gene, e.g., having at least 80%, preferably at least 90%, most preferably at least 95% homology therewith. Especially preferred for use as a SAR in accordance with the present invention is the 800 bp Eco-RI-HindIII (blunt end) fragment of the 5'SAR element of IFN-β as described by Mielke, C et al. Biochemistry 1990 29: 7475–7485.

In a further embodiment, the invention provides:
  (i) a retroviral vector comprising genetic material corresponding to (a) at least one SAR, and (b) at least one heterologous gene operatively linked to an expression control sequence, the heterologous gene (or at least one of the heterologous genes if there is more than one heterologous gene) being rev-M10 and the SAR or at least one SAR is derived from, obtainable from or corresponds to the 5' SAR of the human interferon-β gene;

(ii) a packaging cell line transduced with a retroviral vector according to (i); and (iii) a cellular composition comprising non-immortal eukaryotic cells (preferably a mammalian, e.g., human cell) transduced with a retroviral vector according to (i). Hereinafter (i), (ii) and (iii) above will be referred to as a retroviral vector of the invention, a packaging cell line of the invention and a cellular composition of the invention respectively.

Preferably, the retroviral vector is an amphotropic retroviral vector, preferably a vector characterized in that it has a long terminal repeat sequence (LTR), e.g., a retroviral vector derived from the Moloney murine leukemia virus (MoMLV), myeloproliferative sarcoma virus (MPSV), murine embryonic stem cell virus (MESV). murine stem cell virus (MSCV) or spleen focus forming virus(SFFV). Preferably, in the case of a vector according to (ii), the gene to be expressed replaces the retroviral gag, pol and/or env sequences.

Selection of an appropriate control expression sequences is dependent on the host cell used and the choice is within the skill of one of ordinary skill in the art. Examples of regulatory elements include a transcriptional promoter or enhancer or RNA polymerase binding sequence, sequences conferring inducibility of transcription, and selectable markers may be incorporated into the expression vector. The promoter controlling expression of the gene is, for example viral LTR, e.g., MoMLV LTR, tissue specific promotors, or inducible promoters. Preferably, the construct lacks the retroviral gag, pol and/or env sequences, so that the gag, pol and env functions must be provided in trans by a packaging cell line. Thus, when the vector construct is introduced into the packaging cell, the gag-pol and env proteins produced by the cell assemble with the vector RNA to produce replication-defective, transducing virions that are secreted into the culture medium. The virus thus produced can infect and integrate into the DNA of the target cell, but generally will not produce infectious viral particles since it is lacking essential viral sequences.

Particularly preferred vector structures comprise the general structure Type 1, Type 2 or Type 3:

Type 1: 5' LTR-X-SAR-m-LTR 3';

Type 2: 5' LTR-X-m-SAR-LTR 3';

Type 3: 5' LTR-X-m-LTR/SAR 3';

wherein LTR is a long terminal repeat, X is the gene for the desired protein, preferably the revM10 gene, m is a marker, SAR is a scaffold/matrix attachment region, preferably the hIFNβ SAR described below, and LTR/SAR is a long terminal repeat with SAR incorporated into it, for example the LMSILy (LMSiLy) or LMILy2S (LMiLy2S) vectors further described herein. Alternatively, the vector contains only the gene of interest and one or more SAR elements. In the type 3 vector structure, the SAR element is incorporated into the vector 3' LTR and thereby duplicated into the 5' LTR, resulting in a vector having two copies of the SAR element. Alternatively, two copies of the SAR are arranged to form a vector of structure (5') LTR-X-SAR-m-SAR-LTR (3'). The SAR in a single SAR system, is placed upstream of the 3' LTR. A particularly preferred system is one in which the SAR is in a single copy, in the 3' position (upstream of the 3' LTR) and in reverse orientation. The orientation of the SAR i.e. either forward or reverse is important. In order to increase expression of the heterologous gene, the SAR should be placed (in the vector) in the reverse direction. A SAR in the foreward direction, down-regulates expression. This down-regulation effect is of use in a single SAR-two promoter system for example where lower expression of one gene in a multi-gene system is desired.

The packaging cell line is preferably transfected with separate plasmids encoding gag-pol and env, so that multiple recombination events are necessary before a replication-competent retrovirus (RCR) can be produced. Suitable retroviral vector packaging cell lines include those based on the murine NIH/3T3 cell line and include PA317 (Miller et al. 1986 *Mol. Cell Biol.* 6:2895; Miller et al. 1989 *BioTechniques* 7:980), CRIP (Danos et al. 1988 *Proc. Natl Acad Sci USA* 85:6460), and gp+am12 (Markowitz et al. 1988 *Virology* 167:400); and also cell lines based on human 293 cells or monkey COS cells, for example ProPak A packaging cells, e.g., as described in Pear et al. 1993 *Proc. Natl. Acad. Sci USA* 90: 8392–8396; Rigg et al., 1996 *Virology* 218; Finer et al. 1994 *Blood* 83: 43–50; Landau, et al. 1992 *J. Virol.* 66: 5110–5113). Retroviral vector DNA can be introduced into packaging cells either by stable or transient transfection to produce retroviral vector particles.

The range of host cells that may be infected by a retrovirus or retroviral vector is generally determined by the viral env protein. The recombinant virus generated from a packaging cell can be used to infect virtually any cell type recognized by the env protein provided by the packaging cell. Infection results in the integration of the viral genome into the transduced cell and the consequent stable expression of the foreign gene product. The efficiency of infection is also related to the level of expression of the receptor on the target cell. In general, murine ecotropic env of MoMLV allows infection of rodent cells, whereas amphotropic env allows infection of rodent, avian and some primate cells, including human cells. Xenotropic vector systems utilize murine xenotropic env, and also allow infection of human cells. The host range of retroviral vectors may be altered by substituting the env protein of the base virus with that of a second virus. The resulting, "pseudotyped" virus has the host range of the virus donating the envelope protein and expressed by the packaging cell line. For example, the G-glycoprotein from vesicular stomatitis virus (VSV-G) may be substituted for the MMLV env protein, thereby broadening the host range. Preferably the vector and packaging cell line of the present invention are adapted to be suitable for transduction of human cells.

By heterologous gene is meant a gene which is not a native retroviral gene and which is suitably inserted into the vector under control of a promoter to permit expression in the cell to be transduced. The heterologous gene may be any gene for which expression is desired, e.g., a gene encoding for a protein which interferes with viral or retroviral (e.g., HIV) replication, for example the Rev-M10 gene, e.g., as described in WO 90/14427 and Escaich et al. Hum. Gene Ther. (1995) 6: 625–634.

The eukaryotic cells with which the method of the present invention is employed are non-immortal human cells. By "non-immortal human cell" is meant a human cell which in cell culture will grow through only a finite number of divisions, or which in vivo may undergo maturation or differentiation, e.g., a non-cancerous primary cell. Suitable cell types include cell types which undergo differentiation or activation and which become arrested in vivo, e.g., hematopoietic cells, endothelial cells, fibroblasts, keratinocytes, etc. Accordingly, the present invention encompasses the use of a SAR to increase gene expression in resting (non-proliferating) eukaryotic primary cells, the term resting including cells which were previously active and are now resting. Preferably the cells are non-cancerous hematopoietic cells, e.g., hematopoietic stem cells (for example, CD34+/Thy-1+ cells) or mature hematopoietic cells (e.g., peripheral blood lymphocytes or thymocytes, for example CD4+ cells).

Gene therapy is a method of therapy comprising the use of cells which express heterologous genetic material in vivo. In the case of treatment of an inborn genetic disease characterized by a deficiency in expression of a critical protein (e.g., ADA-deficiency (SCID), hemophilia A and B, Gaucher's disease, and the like), the genetic material is suitably a gene for the normal protein. Alternatively, the gene may be for a protective protein, e.g., a gene for a protein that protects against high dose chemotherapy, e.g., MDR-1, or a gene for a protein protecting against viral or retroviral infection, e.g., rev-M10, or may encode a protective RNA, e.g. a ribozyme or antisense sequence capable of protecting against viral or retroviral infection. Gene therapy may be in vivo, e.g., administering the vector to the patient, so that the target cells are transduced in situ, or ex vivo, e.g., transducing the desired cells in vitro and introducing the transduced cells into the patient, for example a procedure wherein the desired cells are removed and isolated from the individual to be treated, transduced with the desired gene, then reintroduced into the patient.

Peripheral blood lymphocytes (PBLs) have been used as cellular targets for gene therapy applications of immune disorders including SCID-ADA deficiency and HIV disease. At present, retroviral vectors are the gene transfer modality of choice mainly because integration of retrovirally-transduced genes into the chromosome of the target cells supports persistent transgene expression reviewed in. Protocols for efficient gene marking of PBLs have been developed, but little is known about regulation of transgene expression in primary T cells. In vivo, the majority of circulating PBLs are in a resting state and genes encoded by standard retroviral vectors based on the Moloney murine leukemia virus or the Murine embryonic stem cells virus are not efficiently expressed in these cells. The factors that control transgene expression in primary T cells are not known, but may render retroviral-based gene therapy approaches inefficient in certain disease applications including HIV disease.

In a yet further embodiment, the invention provides
(i) a method of gene therapy in a patient in need thereof, comprising introducing into said patient a) a cellular composition of the present invention or b) a retroviral vector of the present invention;
(ii) a cellular composition as described above for therapeutic or prophylactic use, e.g., in a method of gene therapy as described above;
(iii) the use of a SAR or vector as described above in the manufacture of a cellular composition as described above, or in a method of gene therapy as described above.

A preferred embodiment of the present invention is a method of treating a patient suffering from HIV infection, e.g., HIV-1 infection, comprising removing and isolating hematopoietic cells (e.g., hematopoietic stem cells, peripheral blood lymphocytes, CD4+ cells or T cells derived from hematopoietic stem cells) from said patient; transducing the cells with a gene for an anti-retroviral protein (e.g., rev-M10) and a SAR (e.g., a SAR derived or obtainable from the 5' SAR of human IFN-$\beta$), and reintroducing the cells into the patient. Optionally, the patient may receive co-therapy with cytokines or growth factors such as IL-2, and/or with anti-HIV drugs such as AZT, HIV protease inhibitors, or the like.

Mature T-cells isolated from PBL ot thymus (thymocytes) are normally in a resting state (i.e. mitotically inactive). Upon in vitro exposure to various stimuli such as phytomegaglutinin (PHA) and allogenic feeder cells or anti-CD3 and anti-CD28 antibodies the cells become activated and start to proliferate. The activation status of T-cells can be determined measuring expression of the CD25 antigen (IL-2 receptor alpha chain). CD25 expression is low on resting cells and is upregulated on activated cells. After initial activation T-cells will undergo several rounds of division and then return to non-activated state and concomitantly downregulate expression of CD25 antigen.

FIG. 1 depicts schematic representations of the specific retroviral vectors described in the examples. The names of the retroviral vectors are indicated on the left. Vectors are not drawn to scale. LTR is Moloney murine leukemia virus long terminal repeat; MPSV is myeloproliferative sarcoma virus LTR; MESV is murine embryonal stem cell virus LTR; SAR is scaffold or matrix attachment region; IRES is internal ribosomal entry site; NGFr is nerve growth factor receptor.

FIG. 2 depicts expression of retroviral vectors in $CD25^-$ cell populations on day 11 post stimulation.

Figure 4B:
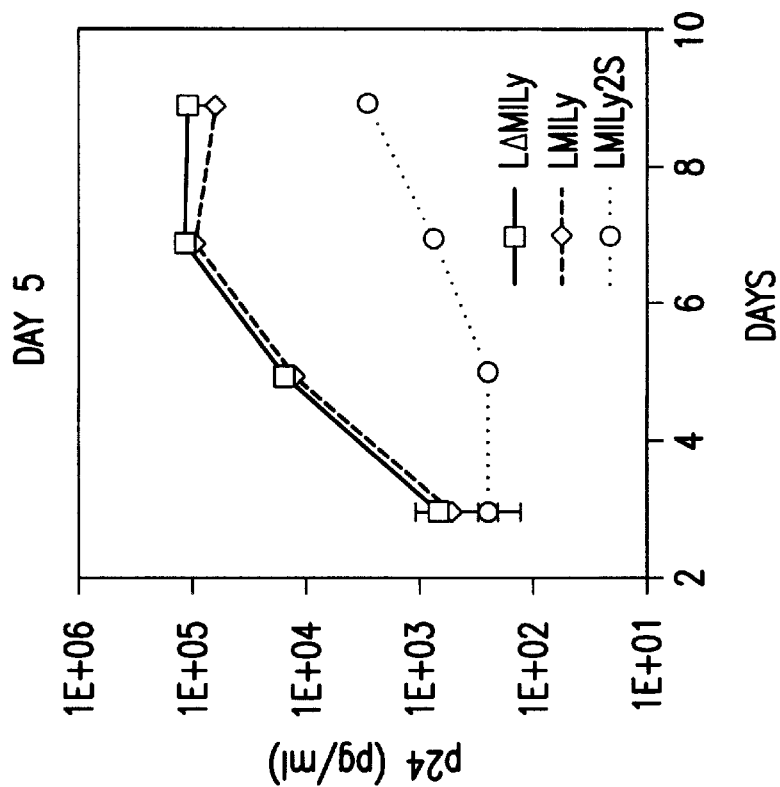
FIGS. 4A and 4B depict the HIV-1 infection experiment. (A) Primary T cells are harvested on day five post-stimulation with PHA, IL-2 and feeder cells and inoculated with the HIV-1 JR-CSF virus. Viral replication is monitored over a period of 9 days by measuring p24 antigen concentration in cell supernatants.

FIG. 4(B) "Day 5 re-stimulated" samples are re-stimulated with fresh PHA, IL-2 and feeder cells on day 3 post inoculation with HIV-1. All values are average from triplicate samples, bars indicate standard error. Where not visible, the error value is below the resolution of the graphics program.

FIG. 5 depicts a comparison of the effect of SAR transduction on the steady state level of retroviral RNA in primary resting T cells and in cultured cells.

Figure 6A:
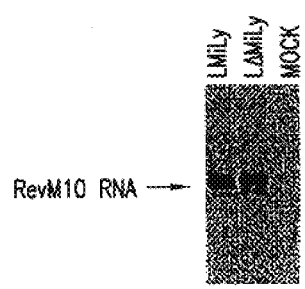
Figure 6B:
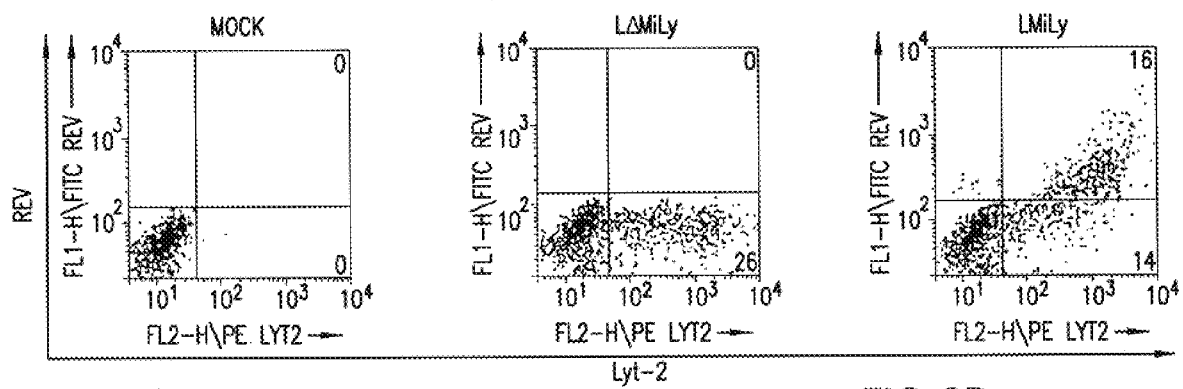

FIGS. 6A and 6B depict RevM10 and Lyt-2 protein expression in LMiLy-transduced CEMSS cells. (A) RevM10 and Lyt-2 protein expression correlate. Northern blot analysis of transduced CEMSS cells. RNA from transduced, Lyt-2-enriched CEMSS cell populations is analyzed using a Rev-specific oligonucleotide probe as described (Plavec, I., et al 1997 *Gene Therapy* 7, 128–139). The transducing vectors are indicated on top. L$\Delta$MiLy is a control vector which does not encode the RevM10 protein ( Plavec, I., et al 1997 *Gene Therapy* 7, 128–139). The genomic size transcripts are indicated by arrow.

FIG. 6(B) CEMSS cells transduced with the indicated vectors and mock transduced control cells are stained with the anti-Lyt-2-PE antibody, fixed in 4% paraformaldehyde and then stained with the anti-Rev-FITC antibody as described (Rigg, R. J., et al 1995 *J. Immunol. Methods* 188, 187–195). The cells used for this analysis are not pre-enriched for Lyt-2 expression. The fraction of transduced cells in these populations determined by Lyt-2 staining is 30% and 26% for LMiLy and LΔMiLy vectors, respectively.

Figure 7:
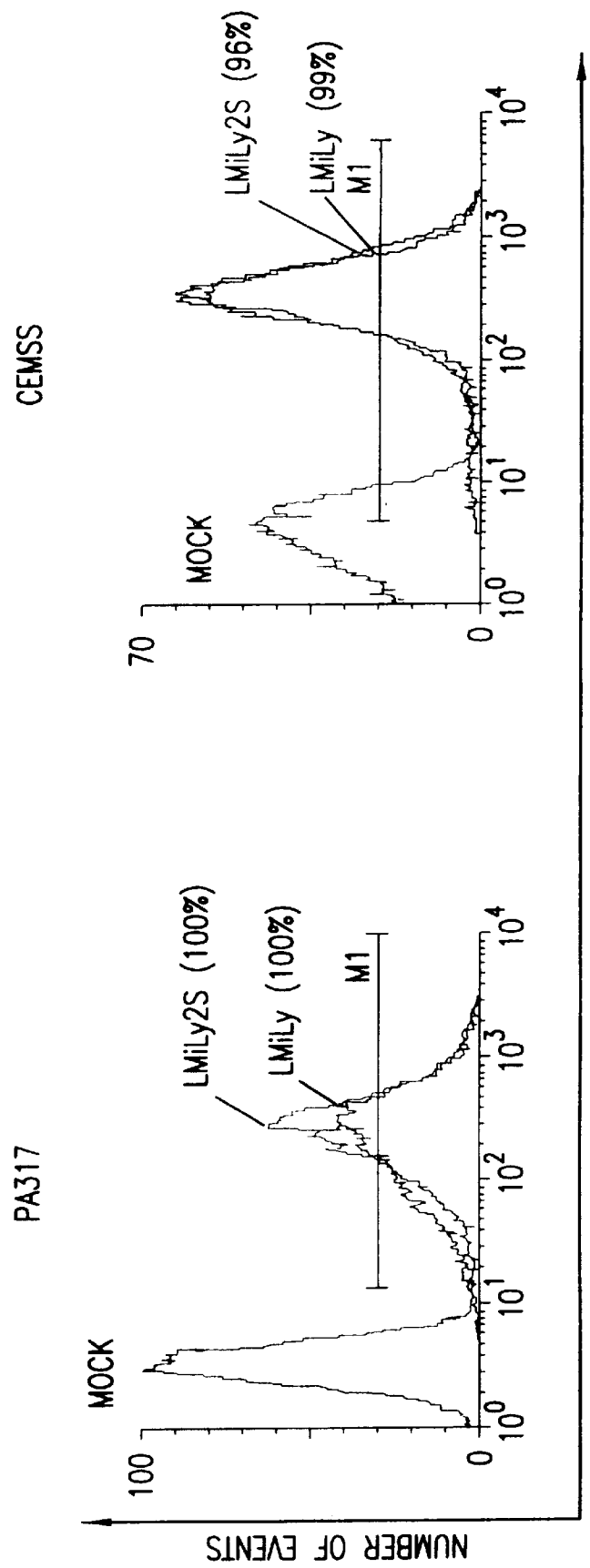

FIG. 7 shows the comparison between LMiLy and LMiLy2S vector expression in transduced cell lines. CEMSS (human CD4+ T cell line) and PA317 (mouse fibroblast line) cells are transduced with the LMiLy and LMiLy2S vectors and Lyt-2-enriched using immunomagnetic beads. The cells are stained with anti-Lyt-2-PE antibody and analyzed by FACscan. The numbers in parenthesis display percentages of Lyt-2-positive cells.

FIGS. 8A–F show that the LMiLy2S vector is efficiently expressed in resting T cells. Lyt-2-enriched LMiLy and LMiLy2S-transduced CD4+ primary T cells are activated with PHA, L-2 and irradiated allogenic feeder cells. On days 3 and 11 post-stimulation, cell aliquots are stained with anti-CD25 FITC and anti-Lyt-2-PE antibodies and analyzed by FACscan. Numbers indicate the percentage of Lyt-2-positive cells in the respective quadrants. Gates for background fluorescence are set based on control isotype antibodies. Mock are untransduced control cells.

Figure 9B:
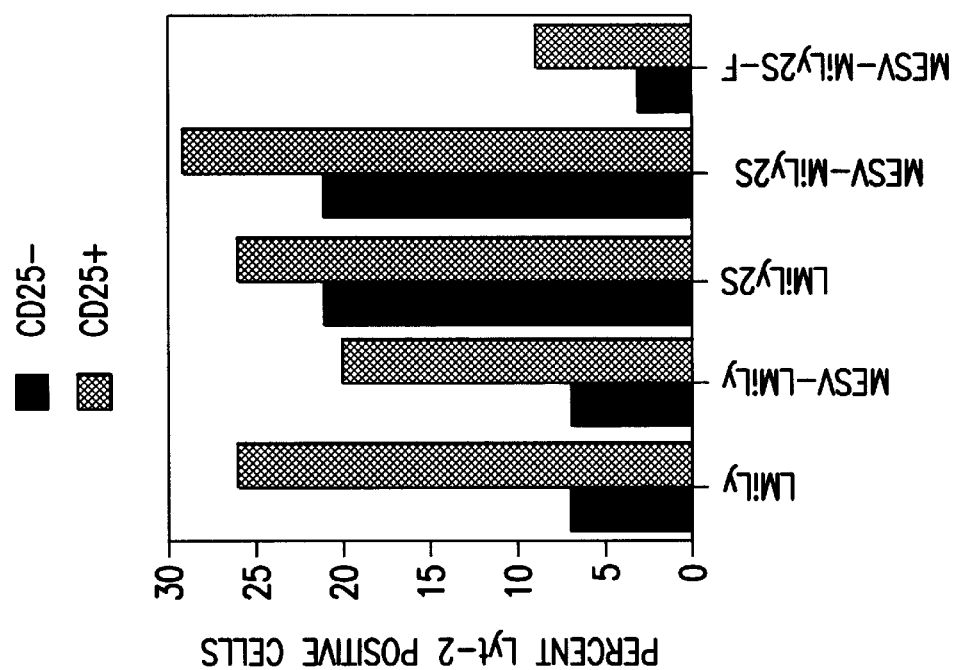
Figure 9A:
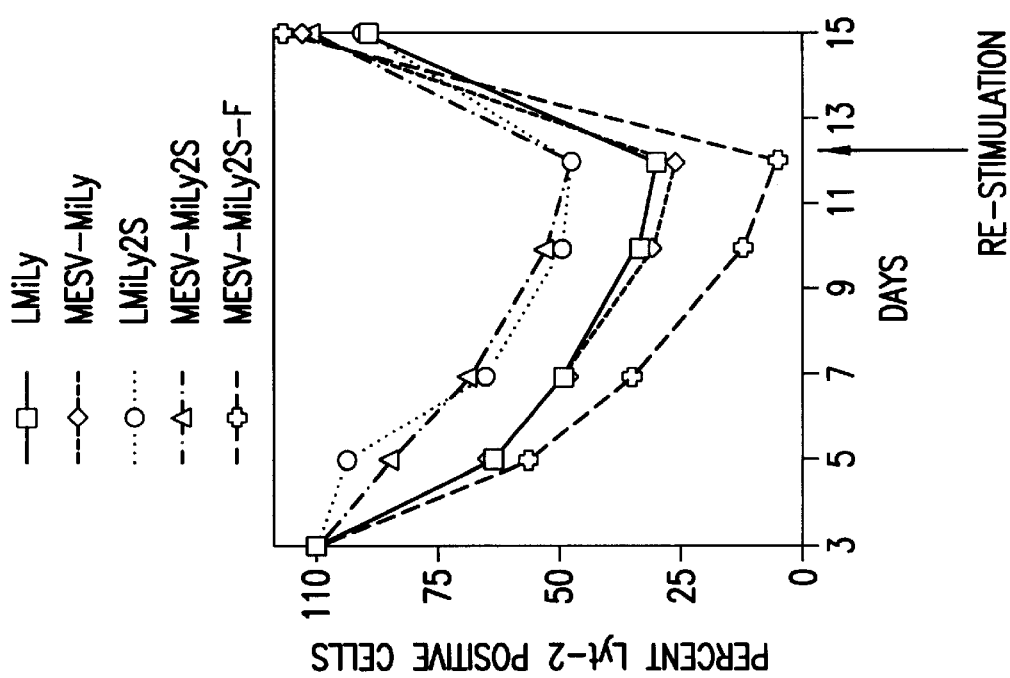

FIGS. 9A and 9B show that the SAR effect is orientation dependent. (A) Lyt-2-enriched CD4+ primary T cells transduced with the MESV-MiLy, MESV-MiLy2S, MESV-MiLy2S-F, LMiLy and LMiLy2S vectors are stimulated with PHA, IL-2 and feeder cells. Transgene expression is analyzed on days 3, 5, 7, 10 and 12 post-stimulation as described in legend to FIG. 2. On day 12, cells are re-stimulated (indicated by arrow) and analyzed three days later (day 15 on the graph). (B) Percentage of Lyt-$2^+$ cells in the $CD25^+$ and $CD25^-$ fractions of resting T cells was determined on day 10 post-stimulation.

EXAMPLE 1: VECTOR CONSTRUCTIONS AND RETROVIRUS-PRODUCING CELLS

Example 1A

Figure 1:
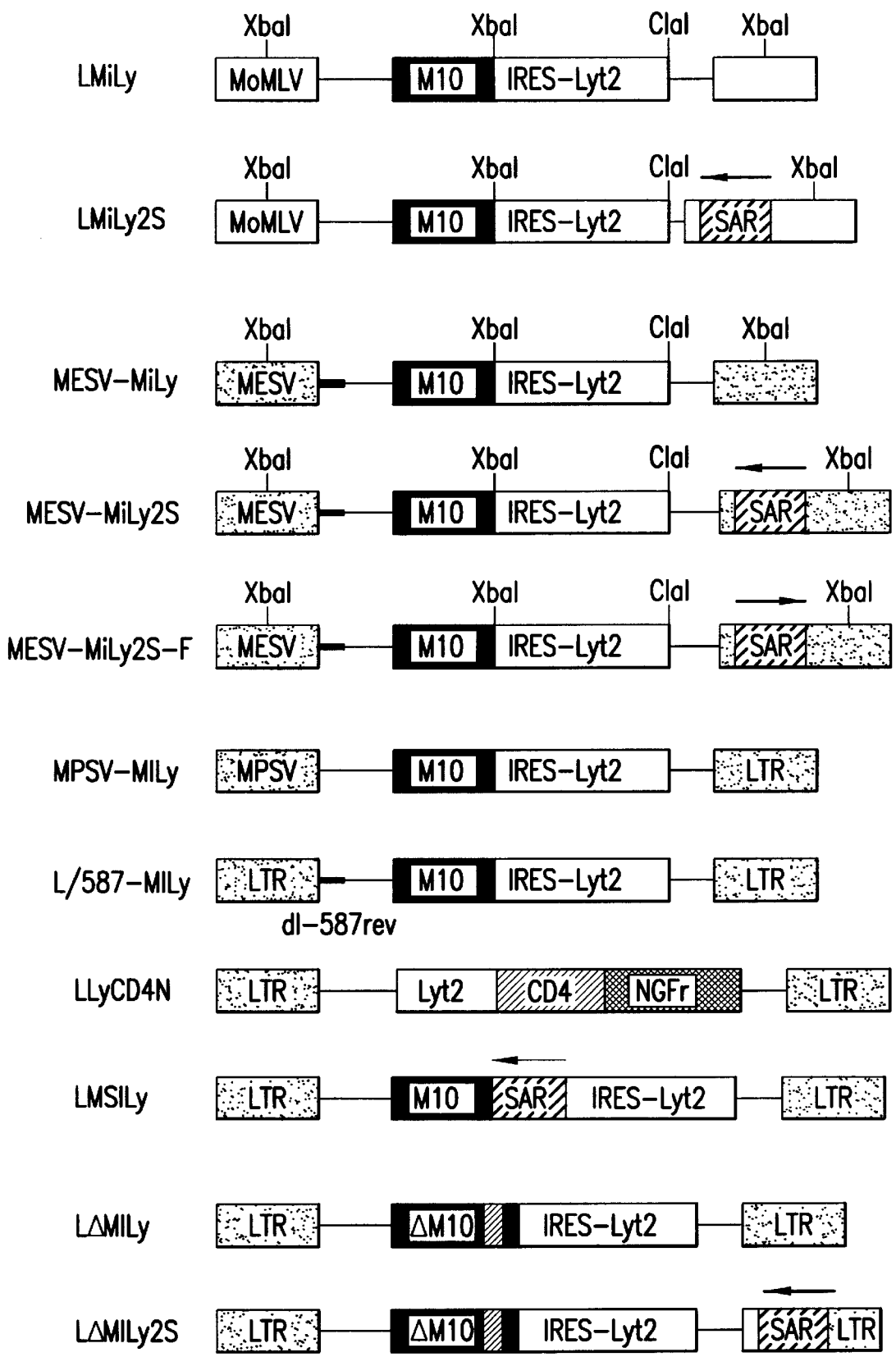

The structures of the recombinant retrovirus vectors are shown in FIG. 1. LMiLy, MESV-MiLy, MPSV-MiLy, L587-MiLy and LMSILy are derived from their MoMLV, MESV, MPSV, MoMLV/587 and MoMLV/SAR counterparts. The XhoI(blunt)-ClaI fragment spanning the tkNeo drug selection marker is exchanged for the BamHI(blunt)-ClaI IRES-Lyt-2 fragment. IRES-Lyt-2 consists of the internal ribosomal entry site (IRES) of the human encephalomyocarditis virus (EMCV) (Jang, S. K. et al. 1989 *J. Virol.* 63:1651–1660) linked to the Lyt-2 α' surface marker gene. Tagawa, M. et al. 1986 *Proc. Natl. Acad. Sci. USA* 83:3422–3426). The LMiLy-2S is constructed by inserting the 800 bp EcoRI-HindIII (blunt end) IFN-β SAR fragment (Klehr, D. et al. 1991 *Biochemistry* 30:1264–1270) into the NheI site in 3' LTR of the LXSN vector, and then the 3' LTR of LMiLy is replaced by SAR-containing 3' LTR from the LXSN. LΔMILY and LΔMILY-2S contain a mutated RevM10 gene (ΔM10) lacking the methionine initiation codon. Escaich, S. et al. 1995 *Hum. Gene Ther.* 6: 625–634. In addition, a 50 bp linker 5'-GATCTGCTACGTG-CATCGCTACCTGACTAGCTGACAGGCCATTCTGGC-CT-3' (SEQ.ID. NO.1) is inserted into the BglII site of the ΔM10 gene (hatched box, FIG. 1). Vector LLyCD4N is constructed by inserting HindIII-ClaI Lyt-2 gene fragment into the EcoRI site of the LXSN (Miller, A.D. et al. 1989 *BioTechniques* 7: 980–990) and then the SV40-Neo fragment of LXSN is replaced by the human nerve growth factor receptor (NGFr) cDNA (1.5 kb BamHI-SacI fragment, Johnson, D. et al. 1986 *Cell* 47:545–554) under control of the human CD4 promoter (1.1 kb fragment, Salmon, P. et al. 1993 *Proc. Natl. Acad. Sci. USA* 90: 7739–7743.). Retroviral vector plasmid DNAs are transfected into BOSC-23 cells as described (Pear, W. S. et al. 1993 *Proc. Natl. Acad. Sci. USA* 90: 8392–8396.). Forty-eight hours post-transfection, BOSC-23 supernatants containing ecotropic retrovirus are used to inoculate PA3 17 cells (Miller, A. D. et al. 1986 *Molecular and Cellular Biology* 6: 2895–2902). Following transduction, Lyt-2-expressing PA317 cells are enriched using fluorescence activated cell sorter (FACS) to generate pools of producer cells. Retroviral vector supernatants are prepared as described in Forestell, S. P. et al. 1995 *Gene Therapy* 2: 723–730. Transduction efficiency of retroviral vector supernatants is determined on NIH3T3 cells. All producer cells are tested for the presence of replication competent retrovirus by S+L–assay on PG4 cells (Haapala, D. K. et al. 1985 *J. Virol.* 53:827–833.).

Example 1B

The MoMLV-based retroviral vector LMiLy (FIG. 1) encodes two genes from one bicistronic mRNA transcript (FIG. 6A).: the RevM10 gene and the Lyt-2 surface marker (mouse CD8 a' chain). Translation of the Lyt-2 protein is mediated by the IRES of the human EMCV and hence, linked to RevM10 protein expression. Double-staining of transduced CEMSS cells for RevM10 and Lyt-2 showed that expression of the two proteins is co-linear (FIG. 6B). Flow cytometric analysis of the easier detectable Lyt-2 surface antigen is subsequently used to estimate overall transgene expression. The 800 bp IFNβ-SAR fragment (as above) is inserted into the NheI site of the 3'LTR of the LMiLy generating the LMiLy2S vector. We have also generated MESV-based vectors because of their advantage over MoMLV for expression in hematopoietic cells. The MESV-MiLy2S and MESV-MiLy2S-F vectors are derived from the MESV-MiLy construct (Plavec I et al, 1997 *Gene Therapy* 7, 128–139.) (FIG. 1). In LMiLy2S and MESV-MiLy2S, the SAR sequence is in the reverse, and in the MESV-MiLy2S-F in the forward orientation, as indicated by the arrows in FIG. 1. Forward and reverse refers to the orientation of the SAR element in its natural human IFNβ gene locus (Junker, U. et al 1995 *Gene Therapy* 2, 639–646). Following transduction, the 3'LTR SAR sequence is duplicated in the 5'LTR generating a double-copy type vector (Hantzopoulos, P. A. et al 1989 *Proc. Natl. Acad. Sci. USA* 86, 3519–3523.). Such double-copy vectors can be unstable (Junker, U., et al 1995 *Gene Therapy* 2, 639–646). Clonal analyses of the LMiLy2S transduced CEMSS cells revealed instability of the vector. In about 30% of individual clonal CEMSS lines integrated proviruses did not contain SAR sequence (data not shown). Amphotropic producer cell lines were generated using ProPak-A packaging cells (Rigg, J. R. et al. 1996 *Virology* 218, 290–295.) Since the vectors do not encode a drug resistance gene it is not possible to determine viral end-point titers. Instead, the ability of viral supernatants to transfer genes into NIH-3T3 cells is measured. Transduction efficiencies (Forestell, S. P., et al (1995) *Gene Therapy* 2, 723–730) of the retroviral stocks used were: LMiLy, 53%; MESV-MiLy, 81%; LMiLy2S, 21%; MESV-MiLy2S, 14%; and MESV-MiLy2S-F, 7%. All retroviral stocks were free of RCR.

EXAMPLE 2: PCR ANALYSIS

For PCR analysis, cell lysates are prepared from 100,000 viable unfractionated or sorted cells. Cells are lysed in 200 μl of a buffer containing 50 mM KCl, I 0 mM Tris pH: 8.3, 2.5 $MgCl_2$, 1% Tween 20, 1% NP40 and 100 mg/ml proteinase K at 56° C. for 2 hours. After lysis, samples are incubated 30 minutes at 95° C. to inactivate proteinase K. Primer used for amplification are: 5' LTR specific primers:
Sar up2+: 5'-TCAATGGGTCTGTTTCTGAGCTCTA-3' (SEQ. ID. NO.2) and
SDdn–: 5'-GGCGCATAAAATCAGTCATAGACAC-3' (SEQ. ID. NO.3); 3' LTR specific primers:
Lyt up+: 5'-ACTTCGCCTGTGATATTTACATCTG-3' (SEQ. ID. NO.4) and LTR dn1–: 5'-TCTATCTGTTCCTGACCTTGATCTG-3' (SEQ. ID. NO.5); and endogenous β-globin gene specific primers:
LA1: 5' ACACAACTGTGTTCACTAGC 3' (SEQ. ID. NO. 6) and
LA2: 5' CAACTTCATCCACGTTCACC 3' (SEQ. ID. NO. 7).

Cells lysates are mixed with the PCR buffer (Perkin Elmer), dNTPs (Pharmacia) 200 μM, 100 pmol of each primer and unit of Taq polymerase (Perkin Elmer). After denaturation (3 minutes at 95° C.), the samples are submitted to 40 cycles of amplification: 1 minute 95° C., 2 minutes 59° C., 2 minutes 72° C., and 10 minutes elongation at 72° C. in thermocycler (Perkin Elmer 4800). PCR products are analyzed by ethidium-bromide staining in 1.4% agarose gels.

EXAMPLE 3: TRANSDUCTION OF PRIMARY T-CELLS

Primary T-cells are isolated either from peripheral blood of healthy donors (PBL) or from thymus grafts of SCID-hu thymus/liver mice (thymocytes) (Plavec, I. et al. 1996 *Gene Therapy* 3, 717–724) and enriched for CD4+ cells by depleting CD8+ cells using anti-CD8 biotinylated Ab (Becton Dickinson) and streptavidin magnetic dynabeads (Dynal). This procedure yields a 90–95% pure CD4+ population. Cells are stimulated to divide in a TOC medium (RPMI supplemented with 1×MEM vitamin solution (GIBCO-BRL), insulin-transferrin-sodium selenite supplement (SIGMA) and 10% fetal bovine serum (Hyclone) with PHA (2 μg/ml), IL-2 (40 U/ml) and allogeneic JY feeder cells (James, S. P. 1994 In Current Protocols in Immunology, vol. 1. R. Coico, editor. John Wiley & Sons, Inc., New York. and Plavec, I. 1997 *Gene Tizerapy* 7, 128–139) for 3–4 days. Retroviral vector transduction is performed by centrifugation of $5 \times 10^5$ cells with 1 ml of supernatant from retroviral producer cells supplemented with 8 μg/ml polybrene for 3 hours at 2000 xg and 34° C. This procedure is performed on two consecutive days. The transduced cells are generally enriched by two rounds of positive selection using anti-Lyt-2 biotinylated Ab (PharMingen) and streptavidin magnetic dynabeads (Dynal) or using fluorescence activated cell sorter (FACS). For analysis of retroviral vector gene expression, cells are stimulated with PHA and feeders as described above and at various time points post-stimulation aliquots of cells are double stained with anti-Lyt-2 R-PE (PharMingen) and anti-CD25 FITC (Beckton Dickinson) antibodies and analyzed on a FACScan (Beckton Dickinson). Expression of NGFr is analyzed using FITC-conjugated anti-NGFr antibody (MoAb 20.4, ATCC#HB8737).

Example 3A

The effect of the SAR sequence on transgene expression is most pronounced in the $CD25^-$ compartment of resting T cells.

Cellular Lyt-2 expression levels (mean fluorescence intensity) of LMiLy- and LMiLy2S-transduced populations are analysed (Table 2). The $CD25^-$ gate is defined using control isotype antibodies (data not shown). On average, there are $5.7 \pm 3.4$ fold more $Lyt-2^+$ cells in the $CD25^-$ fraction of the LMiLy2S than of the LMiLy-transduced populations (Table 2). In contrast, there are only $1.7 \pm 0.5$ fold more $Lyt-2^+$ LMiLy2S- than the LMiLy-transduced cells in the $CD25^+$ fraction (Table 2). The mean fluorescence intensity of the Lyt-2 staining, which is taken as an indirect measure for transgene expression level, is only slightly increased (1.6 fold) in the LMiLy2S compared to the LMiLy-transduced cells and there was no detectable difference between the $CD25^-$ and $CD25^+$ cell fractions (Table 2).

Figure 3A:
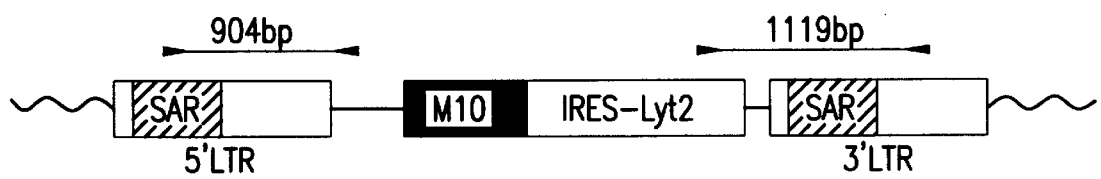
FIG. 3A is a schematic representation of the integrated LMILy2S proviral DNA and the position of primers which are used to amplify SAR sequence present in the 5' and the 3' LTR.
Figure 3B:
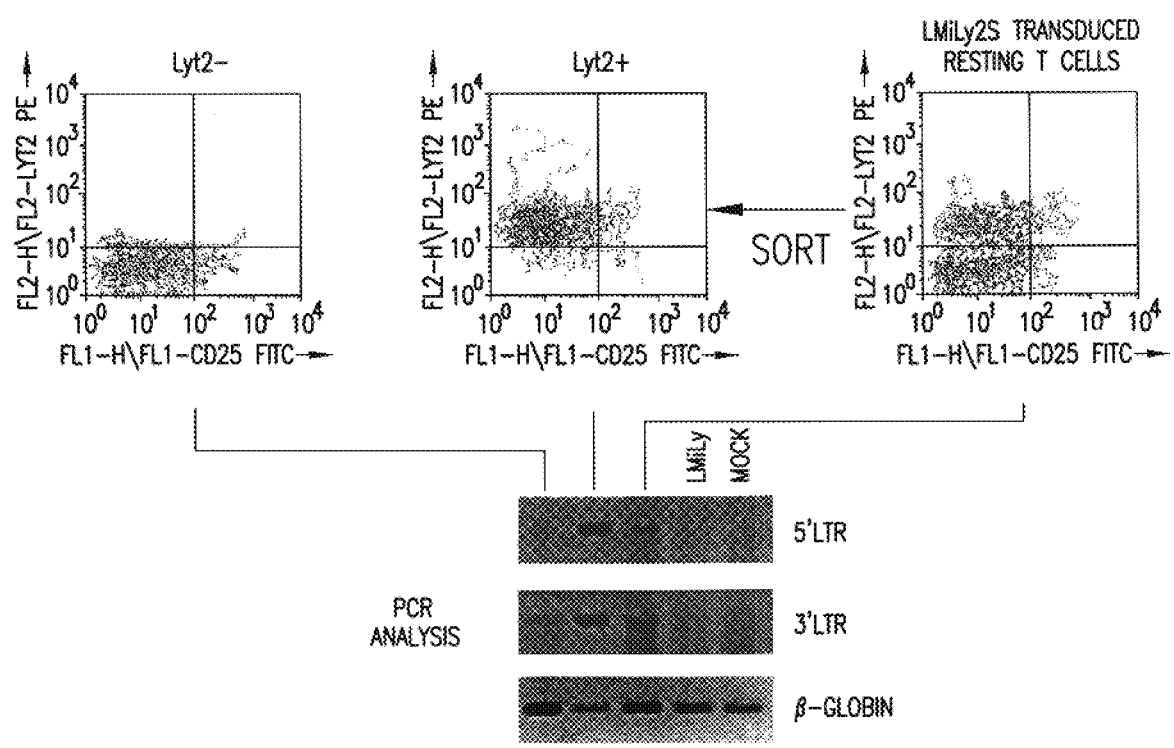
FIG. 3B shows the PCR analysis of the two sorted sub-populations of resting LMiLy2S-transduced T cells, $Lyt-2^+$ and $Lyt-2^-$ cells. The two populations are separated using FACS and analysed by semiquantitative PCR for the presence of the SAR sequence in the proviral DNA.

Two populations of resting LMiLy2S-transduced T cells are observed: 30–40% of the cells are $Lyt-2^+$ and the rest are $Lyt-2^-$ (FIG. 8F.). To further characterise those populations, the $Lyt-2^+$ and the $Lyt-2^-$ cells are separated using FACS and analysed by semiquantitative PCR for the presence of the SAR sequence in the proviral DNA (FIG. 3B). The $Lyt-2^+$ cells show strong SAR-specific PCR signals indicating SAR sequence copies present both in the 5' and the 3' LTR. In contrast, the $Lyt-2^-$ cells yield faint SAR-specific signals implying that a significant portion of integrated retroviral proviruses has lost the SAR sequence, in agreement with our observations about the instability of the LMily2S vector. $Lyt-2^{31}$ cells contain however, transcriptionally competent proviruses as demonstrated by expression of the Lyt-2 marker upon re-stimulation of these cells (data not shown).

TABLE 2

Expression of the Lyt-2 surface marker in the $CD25^-$ and $CD25^+$ subpopulations of resting primary T cells transduced with the LMiLy and LMiLy2S vectors.

| | Percent Lyt-2+ cells | | | | | | Relative transgene expression (Lyt-2 mean fluorescence intensity) | | | | | |
|---|---|---|---|---|---|---|---|---|---|---|---|---|
| | CD25− fraction | | | CD25+ fraction | | | CD25− Lyt-2+ fraction | | | CD25+ Lyt-2+ fraction | | |
| Tissue* | LMiLy | LMiLy2S | Ratio LMiLy2S/LMiLy | LMiLy | LMiLy2S | Ratio LMiLy2S/LMiLy | LMiLy | LMiLy2S | Ratio LMiLy2S/LMiLy | LMiLy | LMiLy2S | Ratio LMiLy2S/LMiLy |
| 1 | 3 | 19 | 6.3 | 12 | 20 | 1.7 | 25 | 41 | 1.6 | 32 | 48 | 1.5 |
| 2 | 1 | 11 | 11 | 6 | 15 | 2.5 | 23 | 35 | 1.5 | 26 | 39 | 1.5 |
| 3 | 7 | 20 | 2.9 | 26 | 28 | 1.1 | 27 | 46 | 1.7 | 44 | 76 | 1.7 |
| 4 | 9 | 22 | 2.4 | 26 | 33 | 1.3 | 23 | 41 | 1.8 | 32 | 54 | 1.8 |
| Average | | | 5.7±3.4 | | | 1.7 ± 0.5 | | | 1.65 ± 0.1 | | | 1.6 ± 0.1 |

Samples are analysed 10–12 days post-stimulation with PHA, IL-2 and allogenic feeder cells. Gates for the $CD25^-$ fractions are set using control isotype antibodies. Quantitative analysis of the Lyt-2 staining was performed when approximately 50% of the total cells fell into the $CD25^-$ gate (see FIG. 8, panel D).
*Tissues 1 and 4 are thymocytes, and 2 and 3 are PBLs.

Example 3B

The SAR sequence enhances transgene expression in an orientation-dependent manner.

The SAR sequence is able to rescue expression of the MESV-based retroviral vector MESV-MiLy (FIG. 1) which is also down-regulated in resting primary T cells (Rigg, J. R.

1996 Virology 218, 290–295). Kinetic analysis of Lyt-2 expression in transduced T cell cultures demonstrates that the MESV-MiLy2S vector behaves similarly to the LMiLy2S vector (FIG. 9A). Compared to MESV-LMiLy, the Lyt-2 transgene is better expressed in the MESV-MiLy2S transduced CD25⁻ resting T cell fraction. Furthermore, the cell number in the Lyt-2⁺CD25⁻ fraction is comparable to the LMiLy2S vector (FIG. 9B). The positive effect is observed only when the SAR sequence is present in the reverse orientation (compare MESV-MiLy2S and MESV-MiLy2S-F vectors, FIG. 9). Interestingly, when the SAR element is in the forward orientation (vector MESV-MiLy2S-F) transgene expression is lower than even with the parental MESV-MiLy vector. Similarly, lower transgene expression is also seen with the LMiLy2S-F vector which carries the SAR sequence in the forward orientation (data not shown).

EXAMPLE 4: HIV INFECTION OF PRIMARY T-CELLS

On day 4–5 following stimulation, cells are washed and resuspended in TOC medium containing IL-2 alone. 2–3× $10^4$ cells in 75 µl volume are mixed with 75 µl of an undiluted JR-CSF HIV-1 virus stock ($10^4$–$10^5$ TCID$_{50}$/ml) and then plated in triplicate in the wells of round-bottom 96-well plates. Cells are cultured overnight and on the following day 125 µl of medium is removed and replaced with 135 µl of fresh TOC+IL-2. In this way cell supernatants are harvested on days 3, 5, 7, and 9 post inoculation. Where indicated, on day three, 135 µl TOC/IL-2 containing 2.5×$10^5$ feeder cells/ml is added to the cells. HIV- I p24 antigen concentration in the culture supernatants is determined using an ELISA kit (Dupont-NEN).

EXAMPLE 5: EXPRESSION OF STANDARD RETROVIRAL VECTORS IN NON-STIMULATED T-CELLS

We have previously observed that the expression of the MoMLV-based retroviral vectors is down regulated in non-stimulated primary human T-cells. We were interested in identifying retroviral vectors which would allow expression in non-stimulated cells. We tested vectors based on myeloproliferative sarcoma virus (MPSV), murine embryonic stem cell virus (MESV), and a MoMLV-based vector which contains a primer binding site from the d1587-rev virus (FIG. 1, vectors MESV-MILy, MPSV-MiLy and L/587-MILy). All these vectors encode Lyt-2 surface marker which allows easy and quantitative analysis of expression (FIG. 1). Primary CD4+ T-cells are stimulated in vitro with PHA, IL-2 and allogeneic feeder cells for 3–4 days and then transduced with retroviral vectors by centrifugation (Bahnson, A. B., et al. (1995) *J. Virol. Methods* 54:131–143). Following this protocol, we detect 4–8% Lyt-2 positive cells and after expansion in vitro, the Lyt-2 positive cells are further enriched to 80–90 % purity using immunomagnetic beads. These cells are then stimulated in a medium containing PHA and feeders. The CD25 surface protein (low affinity IL2 receptor) is used as a marker for the T cell activation status. Three to five days post stimulation, CD25 expression is at a maximum with greater than 95% CD25⁺ cells (FIG. 8A). By days 11 - 14, cells ceased to proliferate and the CD25 marker was down- regulated (>50% CD25⁻ cells ) reflecting the mitotically resting state of these primary T cells (FIG. 8D). Expression of retroviral vectors in stimulated and non-stimulated cultures is determined by staining cells for Lyt2 expression with the anti-Lyt2 antibodies. Results are shown in Table 1A. Expression of Lyt-2 in LMILy, MESV-MILy, MPSV-MILy and U587-MILy transduced cells is down-regulated as the cells become non-stimulated. On day 11 post stimulation, approximately 50% of cells are CD25⁻ and 50% are CD25⁺. The majority of the Lyt-2+ cells are present in CD25⁺ population and very few in the CD25⁻ population. We reasoned that CD25⁻ cells lack transcription factors required for retroviral vector LTR expression. To test this hypothesis a vector is prepared in which expression of a marker gene (in this case it is the human NGF receptor, supra) is driven by the 1.1 kb human CD4 promoter (supra) (FIG. 1, vector LLyCD4N). CD4 molecule is expressed normally at high levels in non-stimulated T-cells. Expression of NGFr from the CD4 promoter in the retrovirally transduced cells, however, is down-regulated in CD25⁻ cells and this down-regulation appears to go in parallel with the down-regulation of the expression of the MoMLV LTR promoter, indicating that the down-regulation is characteristic of the retroviral vector, not the specific promoter used.

TABLE 1A

Expression of retroviral vectors in CD4 + T-cells on day 11 post stimulation.

| Vector | % expressing cells | Mean fluorescence |
|---|---|---|
| LMILy | 6 | 16 |
| LΔMILy | 8 | 16 |
| MESV-MILy | 7 | 18 |
| MPSV-MILy | 2 | 16 |
| L/587-MILy | 7 | 16 |
| LLyCD4N | 9 | 19 |
| LMSILy | 17 | 19 |
| LMILy2S | 23 | 27 |
| LΔMILy2S | 30 | 22 |

TABLE 1B

Expression of the Lyt-2 surface marker in activated and resting primary T cells transduced with the LMiLy and LMiLy2S vectors.

| | Activated | | | Resting | | |
|---|---|---|---|---|---|---|
| | Percent Lyt-2⁺ cells | | | Percent Lyt-2⁺ cells | | |
| Tissue* | LMiLy | LMiLy2S | Ratio LMiLy2S/LMiLy | LMiLy | LMiLy2S | Ratio LMiLy2S/LMiLy |
| 1 | 91 | 96 | 1.05 | 15 | 39 | 2.6 |
| 2 | 65 | 64 | 0.98 | 7 | 26 | 3.7 |

TABLE 1B-continued

Expression of the Lyt-2 surface marker in activated and resting primary T cells transduced with the LMiLy and LMiLy2S vectors.

| | Activated | | | Resting | | |
|---|---|---|---|---|---|---|
| | Percent Lyt-2+ cells | | | Percent Lyt-2+ cells | | |
| Tissue* | LMiLy | LMiLy2S | Ratio $\frac{\text{LMiLy2S}}{\text{LMiLy}}$ | LMiLy | LMiLy2S | Ratio $\frac{\text{LMiLy2S}}{\text{LMiLy}}$ |
| 3 | 73 | 86 | 1.18 | 33 | 48 | 1.5 |
| 4 | 95 | 96 | 1.01 | 35 | 55 | 1.6 |
| Average | | | 1.06 ± 0.08 | | | 2.4 ± 0.9 |

Samples are analyzed on day 3 (Activated) and day 10–12 (Resting) post-stimulation with PHA, IL-2 and allogeneic feeder cells. Gates for the Lyt-2+ cells are set using untransduced T cells as control (see FIG. 8, panels A and D).
*Tissues 1 and 4 are thymocytes, and 2 and 3 are PBLs.

EXAMPLE 6: VECTORS CONTAINING SCAFFOLD ATTACHMENT REGION (SAR) MAINTAIN EXPRESSION IN NON-STIMULATED T-CELLS.

We analysed Lyt-2 transgene expression in activated (day 3 post stimulation ) and resting cells (day 11 post stimulation).

Results obtained with one representative tissue are shown in FIG. 8. There is no marked difference in the percentage of the Lyt-2+ cells between the LMiLy (91 %) and the LMiLy2S (96%) vectors in activated T cells (FIG. 8, panels B and C). In resting cells, overall Lyt-2 expression was lower (FIG. 8, compare panels B and C to E and F), and the loss of transgene expression correlates with the decrease of the CD25 marker. However, we observe a significant difference in Lyt-2 expression between the LMiLy and the LMiLy2S vectors. Fifteen percent of the LMiLy transduced cells are Lyt-2 positive compared to 39% for the LMiLy2S vector (FIG. 8, panels E and F). Upon re-stimulation, both LMiLy- and LMiLy2S-transduced cells express comparable high levels of the Lyt-2 marker (87% and 95%, respectively) demonstrating that the observed loss of expression is not caused by loss of integrated vector (data not shown and FIG. 9A). Similar expression patterns are observed irrespective of the source of primary T cells. The data obtained with four independent tissues (two PBLs and two thymocytes) is summarized in Table IB. Although the absolute percentage of Lyt-2+ resting T cells varies considerably from tissue to tissue, the LMiLy2S vector consistently yields higher values (on average 2.4±0.9 fold more Lyt-2+ cells) than the LMiLy vector (Table 1B).

EXAMPLE 7: INHIBITION OF HIV REPLICATION

Figure 4A:
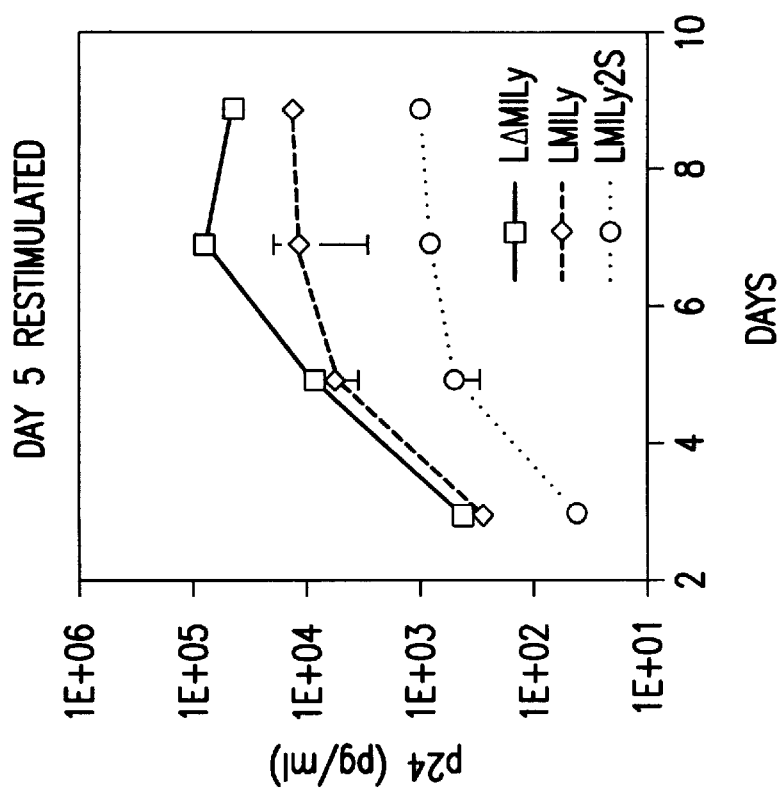

To test whether improved expression would result in more effective RevM10-mediated inhibition of HIV-1 replication, primary CD4+ T cells transduced with the LMiLy, LMSiLy LMiLy2S vectors are inoculated with the HIV- I JR-CSF strain and viral replication is monitored over a period of 9 days (FIG. 4). Cells transduced with the LΔMILy vector which does not produce RevM10 protein (supra) are used as a negative control. Cells are inoculated with HIV-l JR-CSF on day 5 post stimulation with PHA, IL-2 and feeder cells ("Day 5" samples). To make a comparison between stimulated (activated) and non-stimulated (non-activated) cells, on day three post inoculation with HIV, half of the cultures are fed fresh PHA and feeder cells to maintain stimulated phenotype of T-cells. As shown in FIG. 4B. the LMiLy2S vector is not only more potent in inhibiting HIV replication in activated cells but it maintains its efficacy even in resting cells whereas the LMiLy vector lost its anti-viral effect (FIG. 4A). The anti-viral effect of the LMiLy2S vector was solely due to Revel protein expression since a control SAR vector (LΔMiLy2S) which does not encode RevM10 protein had no effect on HIV-1 replication (data not shown). As expected, there was no difference in anti-viral efficacy between the two vectors in HIV-1 HXB-3 infected CEMSS cell populations (data not shown).

EXAMPLE 8: DIFFERENTIAL EXPRESSION IN SAR-TRANSDUCED PRIMARY AND CULTURED CELLS

RNA Analysis: Total Cellular RNA extracted from CEM SS cells (human CD4+ T cells) and thymocytes using Rnazol B (Ambion, Austin Tex.) is analyzed by RNase protection using the Ambion RPA II kit. RNA probes are synthesized using plasmids derived from pBluescriptKS+ (Stratagene) by in vitro transcription with either T3 or T7 polymerase using $^{32}$P-UTP according to the Bluescript Instruction Manual. The RNA probes corresponding to 188 bp HindIII-BamHI fragment internal to the Rev gene and 100 bp PstI-Sall PCR fragment spanning the third exon of the human β-actin gene from positions 1450 to 1550 (GenBank file HUMACTB-CYT-A). The assay is performed by hybridizing≈1 μg total cellular RNA and 9 μg yeast carrier RNA with 1 –2×10$^5$ cpm of each probe. Protected fragments are separated on a 5% polyacrylamide-7 M urea denaturing gel and visualized by autoradiography. Radioactivity in protected fragments is quantitated using a Phosphorimager (Molecular Dynamics). Relative expression of Revel is estimated by using the actin-specific signals as an internal reference to correct for differences in the amount of RNA loaded in different lanes.

We have found that SAR enhances expression of retro-viral vectors in primary T-cells but not in cultured cells (specifically, the CEM SS T-cell line or PA317-mouse fibroblast cell line). CEM SS cells transduced with the LMILy, LMSILy and LMILy2S vectors show patterns of Lyt-2 staining similar to that observed in stimulated or active thymocytes (data not shown). As is shown in FIG. 6 the presence of the SAR element has no effect on transgene expression levels in the established human T cell line nor in the murine cells.

To further analyze the expression of SAR-containing vectors at the molecular level we have isolated total cellular RNA from transduced CEM SS cells and both stimulated and non-stimulated thymocytes. Steady-state level of vector-specific RNA was determined by semiquantitive RNase protection assay. Values obtained in the assay are shown in FIG. 5. Values obtained in CEM SS cells and thymocytes are separately normalized relative to the appropriate LMILy vector RNA. RNA analysis corroborates the results obtained by Lyt-2 staining in primary thymocytes. SAR stimulates the expression of retroviral vectors up to three-fold in both stimulated and non-stimulated thymocytes and again the double SAR configuration is more effective than the single SAR. Interestingly, SAR has no effect on vector RNA expression in transduced CEM SS cells (FIG. 5) underscoring the difference between primary and immortalized T-cells.

What is claimed is:

1. A method of using a DNA scaffold attachment region (SAR) to increase gene expression in retrovirally transduced eukaryotic resting cells comprising,
   (a) transducing eukaryotic cells with a retroviral vector including (i) a heterologous gene operatively linked to an expression control sequence and (ii) a SAR wherein said SAR corresponds to a SAR of the human interferon β gene, a fragment thereof having at least 450 base pairs, or a sequence having 90% homology thereto; and
   (b) allowing said transduced eukaryotic cells to achieve resting state and express the heterologous gene wherein said expression in the transduced eukaryotic resting cells is increased compared to transduction with said vector including said heterologous gene and lacking the SAR.

2. The method according to claim 1 wherein, the SAR is the 5' SAR of the human interferon β gene, a fragment thereof or a SAR having at least 90% homology thereto.

3. The method according to claim 2 wherein, the SAR is the 800 base pair Eco-RI-HindIII blunt end fragment of the 5' SAR human interferon β gene.

4. The retroviral vector of claim 2 wherein, the SAR is the fragment having from 600 to 1000 base pairs of the 5' SAR human interferon β gene.

5. A method of modifying expression of a heterologous gene in a retrovirally transduced eukaryotic cell comprising,
   (a) transducing said eukaryotic cell with a retroviral vector comprising (i) the heterologous gene operatively linked to an expression control sequence and (ii) a scaffold attachment region (SAR) wherein said SAR corresponds to a SAR of the human interferon β gene, a fragment thereof having at least 450 base pairs, or a sequence having 90% homology thereto; and
   (b) allowing expression of the heterologous gene wherein said expression is modified compared to transduction with said vector including said heterologous gene and lacking the SAR.

6. A method of increasing expression of a heterologous gene in a retrovirally transduced eukaryotic resting cell comprising,
   (a) transducing an eukaryotic cell with a retroviral vector comprising (i) the heterologous gene operatively linked to an expression control sequence and (ii) a scaffold attachment region (SAR), wherein said SAR corresponds to a SAR of the human interferon β gene, a fragment thereof having at least 450 base pairs, or a sequence having 90% homology thereto wherein the SAR is in the 3' to 5' direction; and
   (b) allowing said transduced eukaryotic cell to achieve resting state and express said heterologous gene whereby said expression in the transduced eukaryotic resting cell is increased compared to transduction with said vector including said heterologous gene and lacking the SAR.

7. The method according to claim 6 wherein, the cell is a non-cancerous hematopoietic cell.

8. The method according to claim 7 wherein, the cell is a T cell.

9. The method according to claim 6 wherein, the heterologous gene is the rev-M10 gene.

10. The method according to claim 6 wherein, a second SAR element is present in the retroviral vector.

11. The method according to claim 6 wherein the SAR corresponds to the 5'SAR of said human interferon β gene, a fragment thereof having at least 450 base pairs, or a sequence having at least 95% homology thereto.

12. The method according to claim 11 wherein, the SAR is a fragment having from 600 to 1000 base pairs of the 5' SAR human interferon β gene.

13. The method according to claim 11 wherein, the SAR is the 800 base pair Eco-RI-HindIII blunt end fragment of the 5' SAR human interferon β gene.

14. The method according to claim 6 wherein, the SAR is incorporated 3' to the heterologous gene.

15. The method according to claim 6 wherein the retroviral vector further comprises a second heterologous gene.

16. The method according to claim 6 wherein, the retroviral vector comprises a long terminal repeat sequence from a member of the group consisting of moloney murine leukemia virus (MoMLV), myeloproliferative sarcoma virus (MPSV), murine embryonic stem cell virus (MESV), murine stem cell virus (MSCV) and spleen focus forming virus (SFFV).

17. The method according to claim 6 wherein the retroviral vector comprises a long terminal repeat sequence from a lentivirus.

18. The method according to claim 17 wherein the eukaryotic cells are transduced in vitro.

19. The method according to claim 6 wherein the eukaryotic cells are transduced ex vivo.

20. The method according to claim 6 wherein the SAR corresponds to the fragment having from 600 to 1000 base pairs from the 5' SAR of said human interferon β gene or a sequence having at least 95% homology thereto incorporated 3' to the heterologous gene and wherein the vector comprises a long terminal reseat sequence from a moloney murine leukemia virus (MoMLV) or a murine stem cell virus (MSCV).

21. The method according to claim 6 wherein the retroviral vector comprises a long terminal repeat sequence from a moloney murine leukemia virus (MoMLV).

22. The method according to claim 6 wherein the retroviral vector comprises a long terminal repeat sequence from a murine stem cell virus (MSCV).

23. A method of down regulating expression of a heterologous gene in a retrovirally transduced eukaryotic resting cell comprising,
(a) transducing an eukaryotic cell with a retroviral vector comprising (i) the heterologous gene operatively linked to an expression control sequence and (ii) a scaffold attachment region (SAR), wherein said SAR corresponds to a SAR of the human interferon β gene, a fragment thereof having at least 450 base pairs, or a sequence having 90% homology thereto, wherein the SAR is in the 5' to 3' direction, and
(b) allowing said transduced eukaryotic cell to achieve resting state and express said heterologous gene whereby said expression in the transduced eukaryotic resting cell is reduced compared to transduction with said vector including said heterologous gene and lacking the SAR.

24. A method of increasing expression of a heterologous gene in a retrovirally transduced hematopoietic resting cell comprising,
a) transducing a hematopoietic cell with a retroviral vector including (i) a rev-M10 gene operatively linked to an expression control sequence and (ii) a scaffold attachment region (SAR) which corresponds to a SAR of the human interferon β gene, a fragment thereof having at least 450 base pairs or a sequence having 90% homology thereto; and
b) allowing said transduced hematopoietic cell to achieve resting state and express said rev-M10 gene wherein, said retroviral vector comprises a long terminal repeat sequence from a member of the group consisting of moloney murine leukemia virus (MoMLV), myeloproliferative sarcoma virus (MPSV), murine embryonic stem cell virus (MESV), murine stem cell virus (MSCV) and spleen focus forming virus (SFFV) and expression of said rev-M10 gene in the transduced hematopoietic resting cell is increased compared to transduction with said retroviral vector including said rev-M10 gene and lacking the SAR.

25. The method according to claim 24 wherein the hematopoietic resting cells are T-cells.

26. The method according to claim 24 wherein the SAR is placed in the vector in a 3' to 5' orientation.

27. The method according to claim 24 wherein the SAR corresponds to the 5'SAR of the human interferon β gene or a fragment having from 600 to 1000 base pairs of the 5'SAR of the human interferon β gene.

28. The method according to claim 27 wherein the cells are transduced ex vivo.

29. The method according to claim 24 wherein the SAR is placed downstream of the heterologous gene.

30. The method according to claim 24 further comprising a second SAR element in the retroviral vector.

31. The method according to claim 24 wherein the retroviral vector comprises a long terminal repeat sequence from a MoMLV.

32. The method according to claim 24 wherein the retroviral vector comprises a long terminal repeat sequence from a MSCV.

33. The resting cell transduced by the method according to claim 24.

34. A method of increasing expression of a heterologous gene in a retrovirally transduced hematopoietic resting cell comprising,
a) transducing a hematopoietic cell with a retroviral vector including (i) a rev-M10 gene operatively linked to an expression control sequence and (ii) a scaffold attachment region (SAR) which corresponds to a SAR of the human interferon β gene, a fragment thereof having at least 450 base pairs or a sequence having 90% homology thereto; and
b) allowing said transduced hematopoietic cell to achieve resting state and express said rev-M10 gene wherein, said retroviral vector comprises a long terminal repeat sequence from a lentivirus and expression of said rev-M10 gene in the transduced hematopoietic resting cell is increased compared to transduction with said lentiviral vector including said rev-M10 gene and lacking the SAR.

35. A retroviral vector comprising (a) a DNA scaffold attachment region (SAR) corresponding to the 5' SAR of the human interferon β gene, a fragment having at least 450 base pairs thereof, or a homologous SAR having at least 90% homology thereto and (b) a heterologous gene operatively linked to an expression control sequence.

36. The vector according to claim 35 wherein the SAR is the 800 base pair Eco-RI-HindIII blunt end fragment of the 5' SAR human interferon β gene.

37. A method of increasing expression of a heterologous gene in a retrovirally transduced eukaryotic cell comprising,
   (a) transducing an eukaryotic cell with a retroviral vector comprising (i) the heterologous gene operatively linked to an expression control sequence and (ii) a scaffold attachment region (SAR); and
   (b) allowing expression of said heterologous gene whereby said expression in the transduced eukaryotic cell is increased compared to transduction with said vector including said heterologous gene and lacking the SAR.

38. The method according to claim 37, wherein said eukaryotic cell is a hematopoietic cell.

39. The method according to claim 37, wherein said retroviral vector is a lentiviral vector.

40. A method of down regulating expression of a heterologous gene in a retrovirally transduced eukaryotic cell comprising.
   (a) transducing an eukaryotic cell with a retroviral vector comprising (i) the heterologous gene operatively linked to an expression control sequence and (ii) a scaffold attachment region (SAR), and
   (b) allowing down regulation of expression in the transduced cells, whereby said expression in the transduced eukaryotic cell is reduced compared to transduction with said vector including said heterologous gene and lacking the SAR.

41. The method according to claim 40, wherein said eukaryotic cell is a hematopoietic cell.

42. The method according to claim 40, wherein said retroviral vector is a lentiviral vector.

43. A retroviral vector comprising (a) a DNA scaffold attachment region (SAR) and (b) a heterologous gene operatively linked to an expression control sequence.

44. The retroviral vector of claim 43, which vector comprises a long terminal repeat sequence from a member of the group consisting of moloney murine leukemia virus (MoMLV), myeloproliferative sarcoma virus (MPSV), murine embryonic stem cell virus (MESV), murine stem cell virus (MSCV) and spleen focus forming virus (SFFV).

45. The retrovirus vector of claim 43, which is a lentiviral vector.

46. A retroviral vector comprising (a) a DNA scaffold attachment region (SAR) and (b) a heterologous gene operatively linked to an expression control sequence, wherein the heterologous gene is rev-M10 and the SAR corresponds to the 5' SAR of the human interferon β gene, a fragment thereof or a homologous SAR having at least 90% homology thereto.

47. A composition comprising human cells transduced with a retroviral vector as claimed in claim 46.

48. The composition according to claim 47 wherein the cells are hematopoietic cells.

49. The composition according to claim 48 wherein the cells are T cells.

50. The retroviral vector of claim 46 wherein, the retroviral vector comprises a long terminal repeat sequence from a member of the group consisting of moloney murine leukemia virus (MoMLV), myeloproliferative sarcoma virus (MPSV), murine embryonic stem cell virus (MESV), murine stem cell virus (MSCV) and spleen focus forming virus (SFFV).

51. The retroviral vector of claim 46 wherein, the SAR is incorporated 3' to the heterologous gene.

52. The retroviral vector of claim 46 further comprising, a second SAR.

53. The retroviral vector of claim 46 further comprising a second heterologous gene.

* * * * *

SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
      (A) LENGTH: 50 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 1:

GATCTGCTAC GTGCATCGCT ACCTGACTAG CTGACAGGCC ATTCTGGCCT    50

(2) INFORMATION FOR SEQ ID NO: 2:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 2:

TCAATGGGTC TGTTTCTGAG CTCTA    25

(2) INFORMATION FOR SEQ ID NO: 3:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 3:

GGCGCATAAA ATCAGTCATA GACAC    25

(2) INFORMATION FOR SEQ ID NO: 4:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 4:

ACTTCGCCTG TGATATTTAC ATCTG    25

-continued (2) INFORMATION FOR SEQ ID NO: 5:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 5:

TCTATCTGTT CCTGACCTTG ATCTG    25

(2) INFORMATION FOR SEQ ID NO: 6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 6:

ACACAACTGT GTTCACTAGC    20

(2) INFORMATION FOR SEQ ID NO: 7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 7:

CAACTTCATC CACGTTCACC    20